US012765963B2

(12) United States Patent
Tabandeh et al.

(10) Patent No.: US 12,765,963 B2
(45) Date of Patent: Oct. 20, 2026

(54) SYSTEM AND METHOD FOR INTEGRATED MOTION WITH AN IMAGING DEVICE

(71) Applicant: INTUITIVE SURGICAL OPERATIONS, INC., Sunnyvale, CA (US)

(72) Inventors: Saleh Tabandeh, Santa Clara, CA (US); Angel Perez Rosillo, San Francisco, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 780 days.

(21) Appl. No.: 17/607,004

(22) PCT Filed: Apr. 30, 2020

(86) PCT No.: PCT/US2020/030873
§ 371 (c)(1),
(2) Date: Oct. 27, 2021

(87) PCT Pub. No.: WO2020/223569
PCT Pub. Date: Nov. 5, 2020

(65) Prior Publication Data

US 2022/0211460 A1 Jul. 7, 2022

Related U.S. Application Data

(60) Provisional application No. 62/814,627, filed on May 1, 2019.

(51) Int. Cl.
*A61B 90/00* (2016.01)
*A61B 5/06* (2006.01)
(Continued)

(52) U.S. Cl.
CPC ............ *A61B 90/361* (2016.02); *A61B 34/20* (2016.02); *A61B 34/30* (2016.02); *A61B 34/35* (2016.02);
(Continued)

(58) Field of Classification Search
CPC ....... A61B 90/361; A61B 34/20; A61B 34/30; A61B 34/35; A61B 34/70; A61B 34/76;
(Continued)

(56) References Cited

U.S. PATENT DOCUMENTS 10,022,192 B1 * 7/2018 Ummalaneni ......... B25J 9/1694
2008/0234866 A1 * 9/2008 Kishi ..................... A61B 34/37 700/259
(Continued)

FOREIGN PATENT DOCUMENTS

WO WO-2013122889 A1 8/2013
WO WO-2016069648 A1 5/2016
(Continued)

OTHER PUBLICATIONS

Office Action for Chinese Application No. CN202080008186.1, mailed Nov. 20, 2023, 24 pages.
(Continued)

*Primary Examiner* — Sihar A Karwan
(74) *Attorney, Agent, or Firm* — Artegis Law Group, LLP

(57) ABSTRACT

Systems and methods for integrated motion with an imaging device include a device having a first manipulator, a second manipulator, and a controller coupled to the first and second manipulators. When the device is in an imaging device motion mode, the controller is configured to determine whether a first portion of an instrument is located within a viewing region of an image captured by an imaging device; in response to determining that the first portion of the instrument is located within the viewing region, command a
(Continued)

manipulator supporting the instrument to keep a position of a second portion of the instrument fixed relative to the imaging device as the imaging device moves; and in response to determining that the first portion is not within the viewing region, command the manipulator to keep the position of the second portion fixed relative to the workspace as the imaging device moves.

26 Claims, 4 Drawing Sheets

(51) Int. Cl.

| | |
|---|---|
| ***A61B 34/00*** | (2016.01) |
| ***A61B 34/20*** | (2016.01) |
| ***A61B 34/30*** | (2016.01) |
| ***A61B 34/35*** | (2016.01) |
| ***A61B 90/30*** | (2016.01) |
| ***G16H 20/40*** | (2018.01) |
| ***G16H 40/67*** | (2018.01) |
| *A61B 17/00* | (2006.01) |

(52) U.S. Cl.

CPC .............. *A61B 34/70* (2016.02); *A61B 34/76* (2016.02); *A61B 34/77* (2016.02); *G16H 20/40* (2018.01); *G16H 40/67* (2018.01); *A61B 5/067* (2013.01); *A61B 2017/00203* (2013.01); *A61B 2034/2048* (2016.02); *A61B 2034/2057* (2016.02); *A61B 2034/2059* (2016.02); *A61B 2034/2063* (2016.02); *A61B 2034/2065* (2016.02); *A61B 2034/302* (2016.02); *A61B 90/30* (2016.02); *A61B 2090/365* (2016.02); *A61B 2090/371* (2016.02)

(58) Field of Classification Search

CPC ......... A61B 34/77; A61B 5/067; A61B 90/30; A61B 2017/00203; A61B 2034/2048; A61B 2034/2057; A61B 2034/2059; A61B 2034/2063; A61B 2034/2065; A61B 2034/302; A61B 2090/365; A61B 2090/371; G16H 20/40; G16H 40/67

See application file for complete search history.

(56) References Cited

U.S. PATENT DOCUMENTS

| | | | | |
|---|---|---|---|---|
| 2009/0245600 | A1* | 10/2009 | Hoffman | A61B 34/37 348/240.99 |
| 2009/0248036 | A1* | 10/2009 | Hoffman | A61B 1/00149 606/130 |
| 2009/0326322 | A1 | 12/2009 | Diolaiti | |
| 2013/0211588 | A1 | 8/2013 | Diolaiti | |
| 2013/0345718 | A1* | 12/2013 | Crawford | A61B 34/76 606/130 |
| 2015/0297177 | A1* | 10/2015 | Boctor | A61B 34/30 901/47 |
| 2018/0185100 | A1* | 7/2018 | Weinstein | A61F 2/461 |
| 2019/0314097 | A1* | 10/2019 | Diolaiti | B25J 9/1689 |
| 2023/0270510 | A1* | 8/2023 | Diolaiti | A61B 34/37 606/1 |

FOREIGN PATENT DOCUMENTS

| | | | |
|---|---|---|---|
| WO | WO-2016069663 | A1 | 5/2016 |
| WO | WO-2018013979 | A1 | 1/2018 |

OTHER PUBLICATIONS

International Search Report and Written Opinion for Application No. PCT/US2020/030873, mailed on Aug. 20, 2020, 13 pages.

Vertut, J, and Coiffet, P., “Robot Technology: Teleoperation and Robotics Evolution and Development,” English translation, Prentice-Hall, Inc., Inglewood Cliffs, NJ, USA 1986, vol. 3A, 332 pages.

Office Action for Chinese Application No. CN202080008166.1, mailed Aug. 8, 2024, 20 pages.

* cited by examiner

SYSTEM AND METHOD FOR INTEGRATED MOTION WITH AN IMAGING DEVICE

RELATED APPLICATIONS

This application is a U.S. National Stage patent application of International Patent Application No. PCT/US2020/030873, filed Apr. 30, 2020, the benefit of which is claimed, and claims the benefit of U.S. Provisional Application 62/841,627 filed May 1, 2019, each of which is incorporated by reference herein.

TECHNICAL FIELD

The present disclosure relates generally to operation of devices having instruments with end effectors mounted to manipulators and more particularly to operation of the devices to integrate motion of the instruments with motion of an imaging device.

BACKGROUND

More and more devices are being replaced with computer-assisted electronic devices. This is especially true in industrial, entertainment, educational, and other settings. As a medical example, the hospitals of today with large arrays of electronic devices being found in operating rooms, interventional suites, intensive care wards, emergency rooms, and/or the like. For example, glass and mercury thermometers are being replaced with electronic thermometers, intravenous drip lines now include electronic monitors and flow regulators, and traditional hand-held surgical and other medical instruments are being replaced by computer-assisted medical devices.

These computer-assisted devices are useful for performing operations and/or procedures on materials, such as the tissue of a patient, that are located in a workspace. When the workspace is separated from the operator controlling the computer-assisted device, it is common for the operator to control the computer-assisted device using teleoperation and to monitor the activity of the computer-assisted device using an imaging device positioned to capture images or video of the workspace. In computer-assisted devices with instruments that are mounted to repositionable arms and/or manipulators, the teleoperation typically involves the operator using one or more input controls to provide movement commands for the instruments that are, for example, implemented by driving one or more joints in a respective repositionable arm and/or manipulator. In some computer-assisted devices, the imaging device may also be mounted to its own repositionable arm and/or manipulator so that the operator may change a location and/or a direction of a field of view of the imaging device so as to be able to capture images of the workspace from different positions and orientations.

When the imaging device is repositioned and/or reoriented, there are several alternatives for deciding how the instruments mounted to the other repositionable arms and/or manipulators should move in response or not move at all. For example, it is possible to have an instrument move along with the imaging device so that a relative position and/or orientation of the instrument is held fixed relative to the imaging device and, from the perspective of the operator, does not move or shows very little movement in the images captured by the imaging device. In another example, it is possible to have the instrument remain fixed in the workspace so that it does not move despite the movement in the imaging device. There are advantages and disadvantages to both approaches that may affect usability and/or safety of the computer-assisted device.

Accordingly, it would be advantageous to have methods and systems that are able to decide when it is appropriate for an instrument, in response to movement of an imaging device, to move with the imaging device or to remain stationary within a workspace.

SUMMARY

Consistent with some embodiments, a computer-assisted device includes a first manipulator, a second manipulator, and a controller coupled to the first and second manipulators. When the computer-assisted device is in an imaging device motion mode, the first manipulator is supporting a first instrument, the second manipulator is supporting a second instrument, and the first instrument includes an imaging device configured to capture an image of a workspace, the controller is configured to determine whether a first portion of the second instrument is located within a viewing region of the captured image; in response to determining that the first portion of the second instrument is located within the viewing region, command the second manipulator to keep a position of a second portion of the second instrument fixed relative to the imaging device as the imaging device moves; and in response to determining that the first portion of the second instrument is not within the viewing region, command the second manipulator to keep the position of the second portion of the second instrument fixed relative to the workspace as the imaging device moves.

Consistent with some embodiments, a method of operating a computer-assisted device in an imaging device motion mode includes determining whether a first portion of an instrument supported by a first manipulator of the computer-assisted device is located within a viewing region of an image captured by an imaging device supported by a second manipulator of the computer-assisted device; in response to determining that the first portion of the instrument is located within the viewing region, commanding the first manipulator to keep a position of a second portion of the instrument fixed relative to the imaging device as the imaging device moves; and in response to determining that the first portion of the instrument is not within the viewing region, commanding the first manipulator to keep the position of the second portion of the instrument fixed relative to a workspace as the imaging device moves.

Consistent with some embodiments, a non-transitory machine-readable medium including a plurality of machine-readable instructions which when executed by one or more processors are adapted to cause the one or more processors to perform any of the methods described herein.

Figure 1:
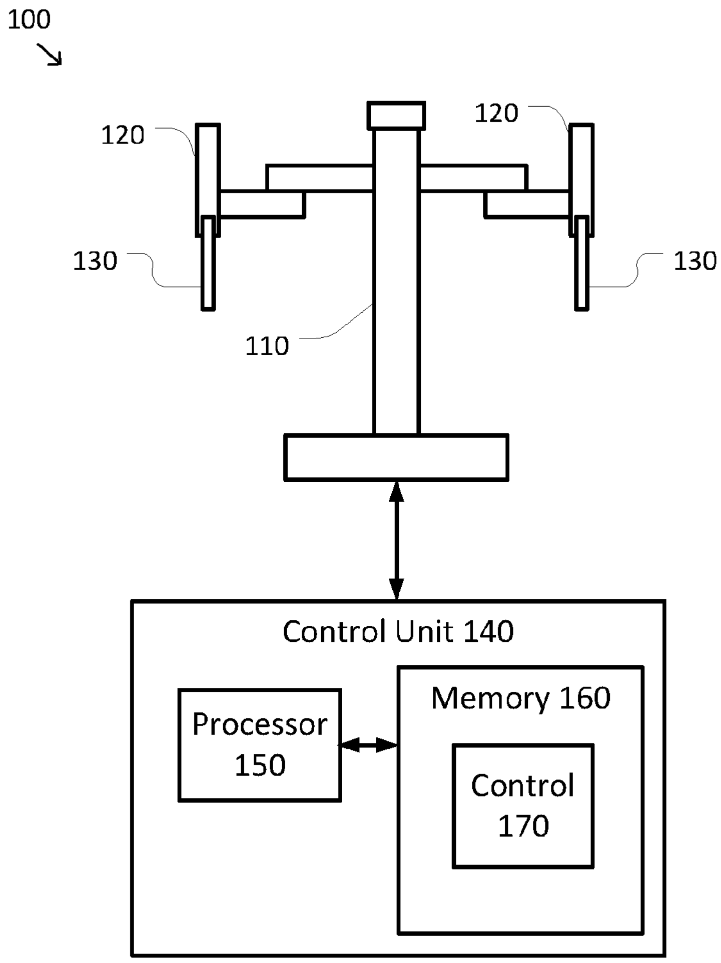
FIG. 1 is a simplified diagram of a computer-assisted system according to some embodiments.

In the figures, elements having the same designations have the same or similar functions.

DETAILED DESCRIPTION

This description and the accompanying drawings that illustrate inventive aspects, embodiments, implementations, or modules should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the elements or their operation in addition to the position and orientation shown in the figures. For example, if the content of one of the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special element positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or module may, whenever practical, be included in other embodiments, implementations, or modules in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

In some instances, well known methods, procedures, components, and circuits have not been described in detail so as not to unnecessarily obscure aspects of the embodiments.

This disclosure describes various devices, elements, and portions of computer-assisted devices and elements in terms of their state in three-dimensional space. As used herein, the term "position" refers to the location of an element or a portion of an element in a three-dimensional space (e.g., three degrees of translational freedom along Cartesian x-, y-, and z-coordinates). As used herein, the term "orientation" refers to the rotational placement of an element or a portion of an element (three degrees of rotational freedom—e.g., roll, pitch, and yaw). As used herein, the term "shape" refers to a set positions or orientations measured along an element. As used herein, and for a device with repositionable arms, the term "proximal" refers to a direction toward the base of the computer-assisted device along its kinematic chain and "distal" refers to a direction away from the base along the kinematic chain.

Aspects of this disclosure are described in reference to computer-assisted systems and devices, which may include systems and devices that are teleoperated, remote-controlled, autonomous, semiautonomous, robotic, and/or the like. Further, aspects of this disclosure are described in terms of an implementation using a surgical system, such as the da Vinci® Surgical System commercialized by Intuitive Surgical, Inc. of Sunnyvale, California. Knowledgeable persons will understand, however, that inventive aspects disclosed herein may be embodied and implemented in various ways, including robotic and, if applicable, non-robotic embodiments and implementations. Implementations on da Vinci® Surgical Systems are merely exemplary and are not to be considered as limiting the scope of the inventive aspects disclosed herein. For example, techniques described with reference to surgical instruments and surgical methods may be used in other contexts. Thus, the instruments, systems, and methods described herein may be used for humans, animals, portions of human or animal anatomy, industrial systems, general robotic, or teleoperational systems. As further examples, the instruments, systems, and methods described herein may be used for non-medical purposes including industrial uses, general robotic uses, sensing or manipulating non-tissue work pieces, cosmetic improvements, imaging of human or animal anatomy, gathering data from human or animal anatomy, setting up or taking down systems, training medical or non-medical personnel, and/or the like. Additional example applications include use for procedures on tissue removed from human or animal anatomies (without return to a human or animal anatomy) and for procedures on human or animal cadavers. Further, these techniques can also be used for medical treatment or diagnosis procedures that include, or do not include, surgical aspects.

FIG. 1 is a simplified diagram of a computer-assisted system 100 according to some embodiments. As shown in FIG. 1, computer-assisted system 100 includes a device 110 with one or more repositionable arms 120. Each of the one or more repositionable arms 120 may support one or more instruments 130. In some examples, device 110 may be consistent with a computer-assisted medical device. The one or more instruments 130 may include non-imaging instruments, imaging devices, and/or the like. In some medical examples, the instruments may include medical instruments, such as clamps, grippers, retractors, cautery instruments, suction instruments, suturing devices, and/or the like. In some medical examples, the imaging devices may include endoscopes, cameras, ultrasonic devices, fluoroscopic devices, and/or the like. In some examples, each of the one or more instruments 130 may be inserted into a workspace (e.g., anatomy of a patient, a veterinary subject, and/or the like) through a respective cannula docked to a respective one of the one or more repositionable arms 120. In some examples, a direction of a field of view of an imaging device may correspond to an insertion axis of the imaging device and/or may be at an angle relative to the insertion axis of the imaging device. In some examples, each of the one or more instruments 130 may include an end effector that may be capable of both grasping a material (e.g., tissue of a patient) located in the workspace and delivering energy to the grasped material. In some examples, the energy may include ultrasonic, radio frequency, electrical, magnetic, thermal, light, and/or the like. In some embodiments, computer-assisted system 100 may be found in an operating room and/or an interventional suite. In some examples, each of the one or more repositionable arms 120 and/or the one or more instruments 130 may include one or more joints.

Device 110 is coupled to a control unit 140 via an interface. The interface may include one or more cables, connectors, and/or buses and may further include one or more networks with one or more network switching and/or routing devices. Control unit 140 includes a processor 150 coupled to memory 160. Operation of control unit 140 is controlled by processor 150. And although control unit 140 is shown with only one processor 150, it is understood that processor 150 may be representative of one or more central processing units, multi-core processors, microprocessors, microcontrollers, digital signal processors, field programmable gate arrays (FPGAs), application specific integrated circuits (ASICs), graphics processing units (GPUs), tensor processing units (TPUs), and/or the like in control unit 140. Control unit 140 may be implemented as a stand-alone subsystem and/or as a board added to a computing device or as a virtual machine.

Memory 160 may be used to store software executed by control unit 140 and/or one or more data structures used during operation of control unit 140. Memory 160 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 160 includes a control module 170 that is responsible for controlling one or more aspects of the operation of computer-assisted device 110 so that motion of the one or more instruments 130 is integrated with the motion of an imaging device used to capture images of the operation of the one or more instruments as is described in further detail below. And although control module 170 is characterized as a software module, control module 170 may be implemented using software, hardware, and/or a combination of hardware and software.

As discussed above and further emphasized here, FIG. 1 is merely an example which should not unduly limit the scope of the claims. One of ordinary skill in the art would recognize many variations, alternatives, and modifications. According to some embodiments, computer-assisted system 100 may include any number of computer-assisted devices with articulated arms and/or instruments of similar and/or different in design from computer-assisted device 110. In some examples, each of the computer-assisted devices may include fewer or more articulated arms and/or instruments.

Figure 2:
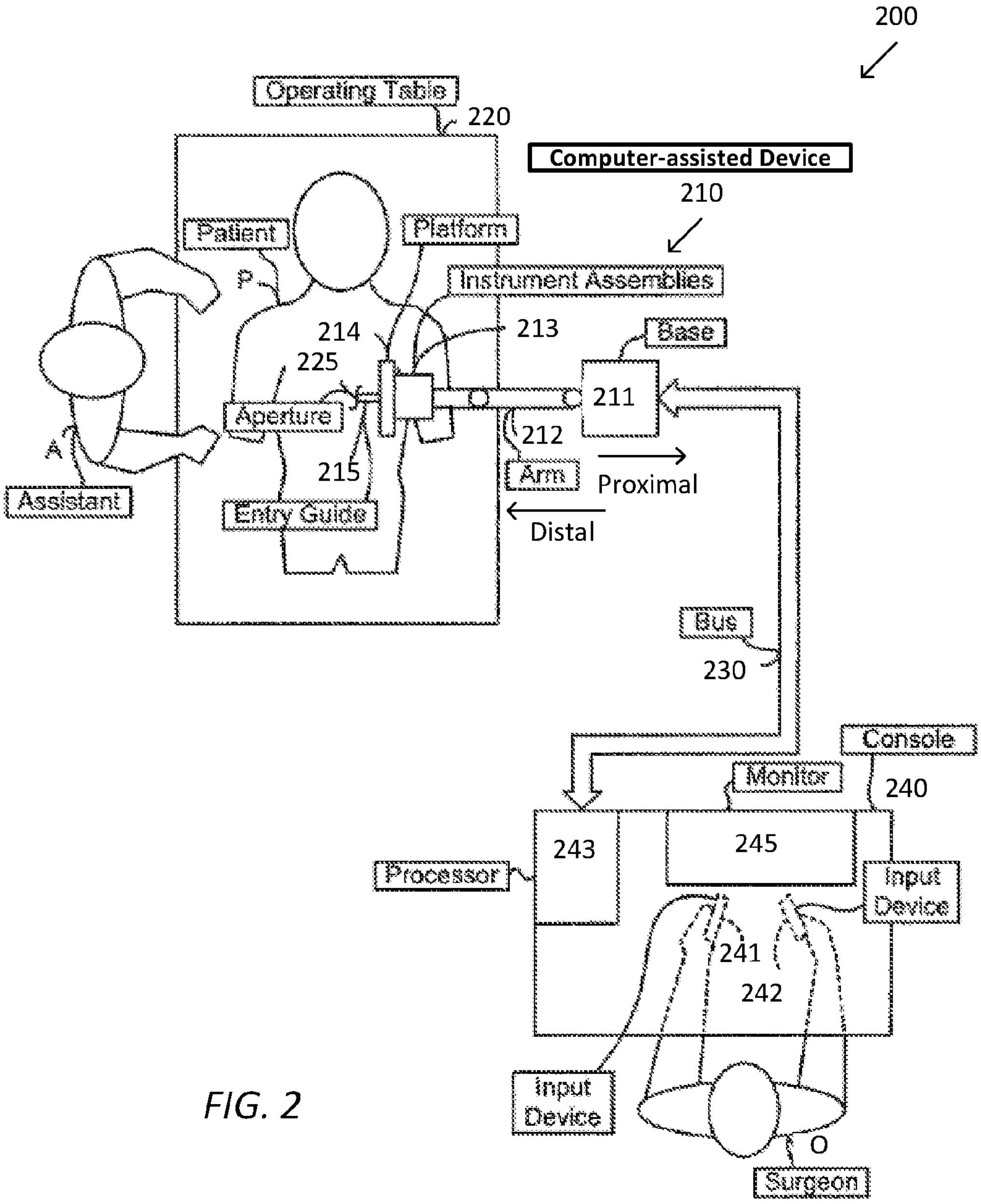
FIG. 2 is a simplified diagram of a computer-assisted device according to some medical embodiments.

FIG. 2 is a simplified diagram of a computer-assisted system 200 according to some medical embodiments. In some embodiments, computer-assisted system 200 may be consistent with computer-assisted system 100. As shown in FIG. 2, computer-assisted device 200 includes a computer-assisted device 210, which may be consistent with computer-assisted device 110. Computer-assisted device 210 includes a base 211 located at a proximal end of a kinematic chain for computer-assisted device 210. During a procedure, computer-assisted device 210 and base 211 may be positioned adjacent to a workspace, such as a patient P as shown in FIG. 2. A repositionable arm 212 is coupled to base 211. In some examples, repositionable arm 212 may include one or more joints for changing a position and/or an orientation of a distal end of repositionable arm 212 relative to base 211. A set of instrument assemblies 213 is mounted toward the distal end of repositionable arm 212. Each of the instrument assemblies 213 may be used to control a respective instrument (not shown). The instrument assemblies 213 are attached to a platform 214, which supports an entry guide 215 through which the instruments are passed to gain access to a worksite. The worksite corresponds to the interior anatomy of patient P in the examples of FIG. 2. Patient P is located on a surgical table 220 and the access to the interior anatomy of patient P is obtained through an aperture 225, such as an incision site on patient P and/or a natural body orifice of patient P. In some examples, access through the aperture 225 may be made through a port, a cannula, a trocar, and/or the like. In some examples, the worksite may correspond to exterior anatomy of patient P, or a non-patient related worksite.

Also shown in FIG. 2 is an operator console 240 coupled to computer-assisted device 210 through a bus 230. In some examples, bus 230 may be consistent with the interface between control unit 140 and computer-assisted device 110 in FIG. 1. Operator console includes two input devices 241 and 242, which may be manipulated by an operator O (e.g., a surgeon as shown) to control movement of computer-assisted device 210, arm 212, instrument assemblies 213, the instruments, and/or the like through, for example, teleoperational control. Operator console 240 further includes a processor 243, which may be consistent with control unit 140 and/or processor 150. To aid operator O in the control of computer-assisted device 210, operator console 240 further includes a monitor 245, which is configured to display images and/or video of the worksite captured by an imaging device. In some examples, monitor 245 may be a stereoscopic viewer. In some examples, the imaging device may be one of the instruments of the computer-assisted device, such as an endoscope, a stereoscopic endoscope, and/or the like. Operator O and/or computer-assisted device 210 may also be supported by a patient-side assistant A.

Figure 3:
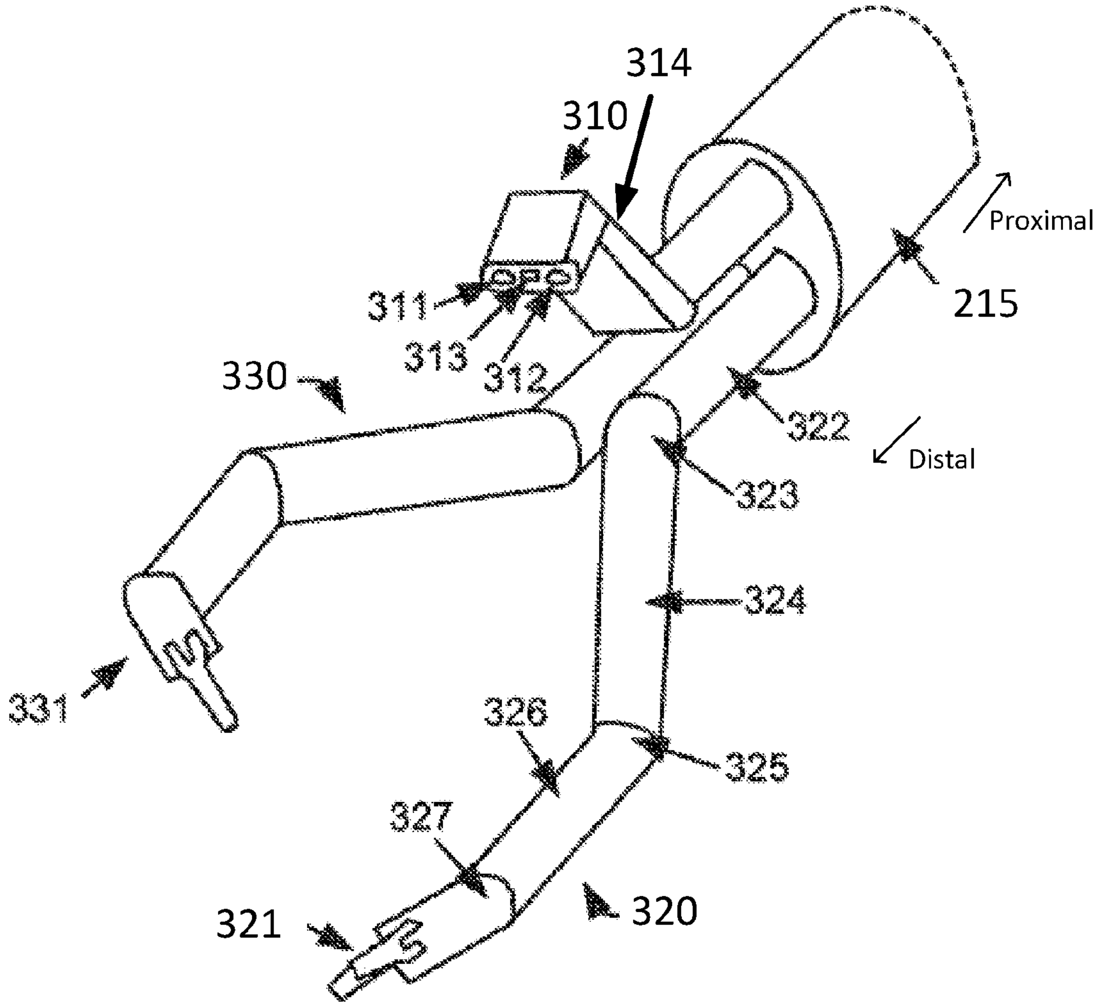
FIG. 3 is a simplified diagram of a distal end of a computer-assisted device having an imaging device and multiple instruments according to some medical embodiments.

FIG. 3 is a simplified diagram of a distal end of a computer-assisted device having an imaging device and multiple instruments according to some medical embodiments. In some embodiments, the computer-assisted device may be consistent with computer-assisted device 110 and/or 210. As shown in FIG. 3, the distal end of the computer-assisted device includes entry guide 215 through which an instrument 310 comprising an imaging device (also referred to as "imaging device 310") and two instruments 320 and 330 may be inserted to, or otherwise placed at, a worksite. For convenience of explanation in this application, when discussing movement of an instrument relative to an instrument with the imaging functionality used for providing the viewing region, the instrument used for providing the viewing region may be referred to as the "imaging device" and the instrument referred to as the "instrument" (even though this instrument may also include imaging functionality). In the examples of FIG. 3, imaging device 310 utilizes optical technology and includes a pair of stereoscopic image capturing elements 311 and 312 and an illumination source 313 for illuminating the worksite. In some examples, the illumination source 313 may be located in a distal portion of imaging device 310 and/or may be located proximal to imaging device 310 with the illumination guided to the distal end via a fiber optic cable. In some examples, the imaging device utilizes other imaging modalities that may or may not require an illumination source, such as ultrasonic imaging. Imaging device 310 further includes a repositionable structure 314, which may include one or more joints and links for changing a position and/or an orientation of the distal portion of imaging device relative to entry guide 215.

Instruments 320 and 330 also include respective repositionable structures with respective end effectors 321 and 331 located at their respective distal portions. As a representative example, the repositionable structure of instrument 320 is shown with various joints and links 322-327. Like imaging device 310, the distal portions of instruments 320 and 330 (e.g., end effectors 321 and 331, respectively) may have their positions and/or orientations relative to entry guide 215 changed through manipulation of the repositionable structures.

The examples of computer-assisted devices 110 and/or 210 in FIGS. 1-3 illustrate that the links and joints used to control the positions and/or orientations of the distal portions of the instruments 130, 310, 320, and/or 330 may be classified into two types of links and joints. The first type of links and joints are shared (sometimes referred to as common-mode) links and joints. Shared links and joints have the characteristic that manipulation of the shared links and joints (e.g., by articulating the shared joints with respective actuators) repositions and/or reorients two or more of the instruments and/or the distal portions of the instruments as a combined unit. This is because the shared links and joints are coupled in series with the kinematic chains specific to the two or more instruments, and the shared links and joints are located proximal to the two or more instruments. Examples of shared links and joints from FIGS. 1-3 include the links and joints in a base and vertical column of computer-assisted device 110, the links and joints of base 211, and/or the links and joints of repositionable arm 212.

The second type of links and joints are independent (sometimes referred to as differential mode) links and joints. Independent links and joints have the characteristic that manipulation of the independent links and joints (e.g., by articulating the independent joints with respective actuators) repositions and/or reorients only the instrument and/or the distal portion of the instrument with which they are associated. This is because the independent links and joints are located on only the kinematic chain of their respective instrument. Examples of independent links and joints from FIGS. 1-3 include the links and joints in repositionable arms 120, the links and joints in instruments 130, the links and joints of repositionable structure 314 of imaging device 310, and/or the links and joints of the repositionable structures of instruments 320 and/or 330.

During a procedure with a computer-assisted device, an operator (e.g., operator O) may find it advantageous to reposition and/or reorient an imaging device (e.g., imaging device 310) to obtain a different view of and/or a view of different portions of a worksite in a workspace. When the imaging device is repositioned and/or reoriented in the workspace, there are several alternatives for deciding how parts of the other instruments (e.g., instruments 320 and/or 330) located in the workspace should move or not move in response. For example, it may be desirable to have a part and/or the entirety of an instrument move along with or follow the imaging device so that a relative position and/or orientation of the instrument is held fixed relative to the imaging device and, from the perspective of the operator, does not move or shows very little movement in the images captured by the imaging device. In some examples, a distal portion of the instrument, a clevis of a jawed instrument, an end effector of the instrument, a wrist of the instrument, and/or a tip of the instrument moves along with, or follows, the imaging device. This approach has the advantage that the operator does not have to separately reposition and/or reorient the instrument and the instrument moves toward the new view of the worksite. This, however, is not without disadvantages; for example, as the instrument moves, it may collide with one or more objects in the workspace and, when the instrument is not observable in the images captured by the imaging device, the operator may not be aware of these collisions. In medical examples, this could result in injury to a patient when the instrument collides with anatomy.

As another example, it may be desirable for a part and/or the entirety of the other instrument to remain fixed or held still in the workspace so that it does not move despite the movement of the imaging device. This may reduce the likelihood of unintended instrument motion and be less likely to be involve a collision, but may not be as efficient or convenient for the operator. In addition, when the imaging device and the instrument have one or more shared joints and links, and the motion of the imaging device includes motions of the shared joints and links, this approach may limit the range of movement that the imaging device can make. For example, as the one or more shared joints and links move to move the imaging device, the independent joint(s) of the instrument move to keep the part of the instrument (e.g., the tip) fixed in the workspace. This may limit the movement that the imaging device may make before one or more range of motion limits for the independent joints of the instrument are reached and the part of instrument can no longer remain fixed in the workspace if further imaging device motion occurs.

One criterion for determining whether to allow the instrument to follow the motion of the imaging device is whether the instrument is within the viewing region of the imaging device, indicating that it is possible for the operator to monitor the movement of the instrument as it follows the motion of the imaging device. Various tests for determining whether the instrument is within the viewing region are described in further detail below.

Figure 4:
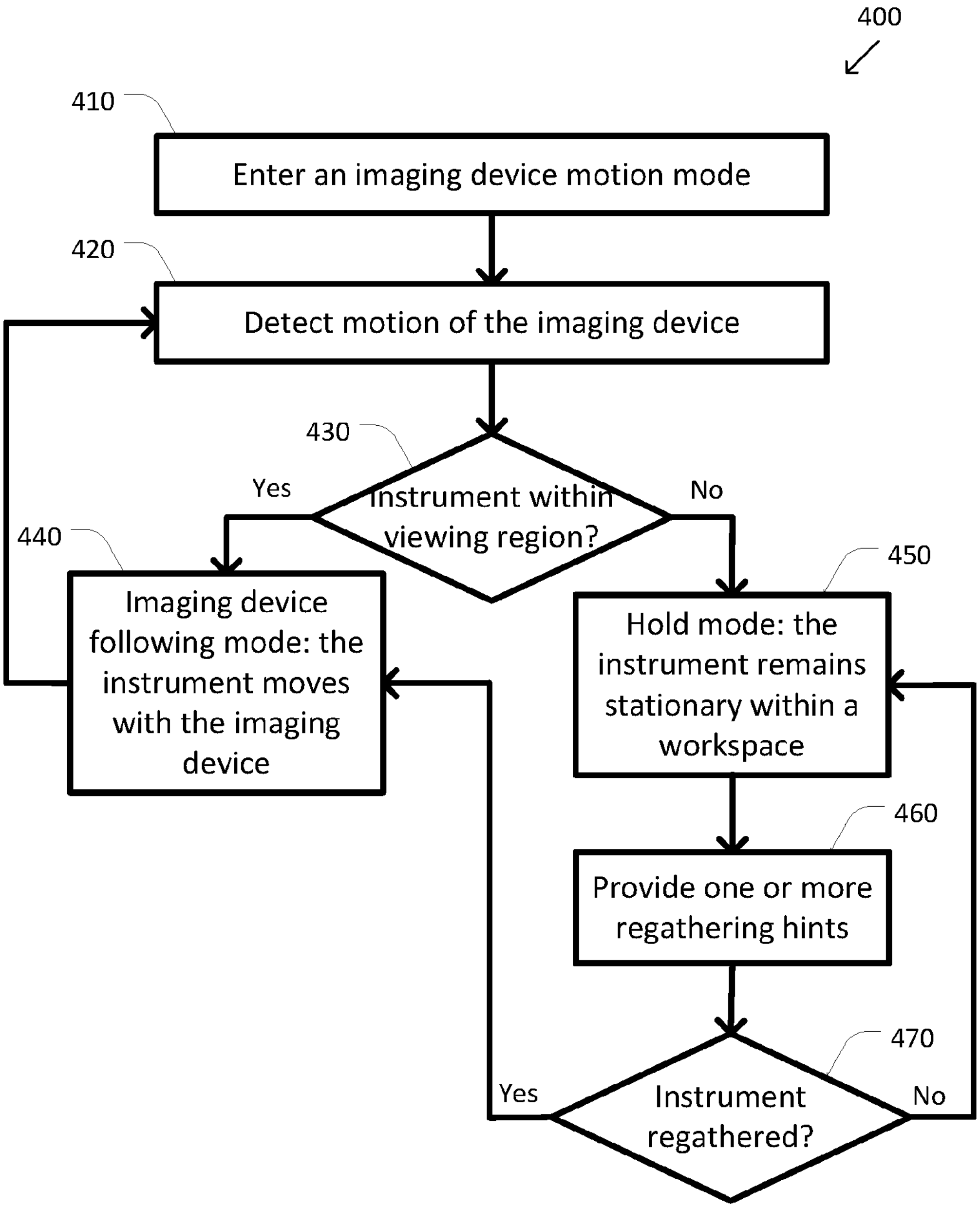
FIG. 4 is a simplified diagram of a method of integrating instrument motion with imaging device motion according to some embodiments.

FIG. 4 is a simplified diagram of a method 400 of integrating instrument motion with imaging device motion according to some embodiments. One or more of the processes 410-470 of method 400 may be implemented, at least in part, in the form of executable code stored on non-transitory, tangible, machine readable media that when run by one or more processors (e.g., the processor 150 in control unit 140 and/or processor 243) may cause the one or more processors to perform one or more of the processes 410-470. In some embodiments, method 400 may be performed by one or more modules, such as control module 170. In some embodiments, method 400 may be used to automatically and/or semi-automatically control motion of an instrument (e.g., instrument 130, 320, and/or 330) when motion of an imaging device (e.g., imaging device 310) is detected. In some embodiments, process 460 is optional and may be omitted.

In some embodiments, method 400 may be performed in a different order than the order implied by FIG. 4. In some examples, process 420 may be performed concurrently with one or more of processes 430-470 so that motion of the imaging device and the response of the system to that motion occurs continuously throughout method 400. In some embodiments, method 400 may be performed separately and/or in parallel for each of two or more instruments.

At a process 410, an imaging device motion mode is entered. In some examples, the imaging device motion mode may be entered in response to one or more commands received from an operator, such as operator O or assistant A. In some examples, the one or commands may be associated with the activation of a user interface control at an operator console, such as operator console 240. In some examples, the user interface control may include a button, a switch, a lever, a pedal, and/or the like that is mechanically activated (or deactivated) by the operator. In some examples, the user interface control may be a control on an interface display displayed to the operator, such as an interface display shown on monitor 245. In some examples, the one or more commands may be associated with a voice command, a gesture, and/or the like made by the operator. In some examples, the imaging device motion mode corresponds to a mode where one or more repositioning and/or reorienting commands for the imaging device are received from the operator, such as may occur when the operator teleoperates the imaging device using one or more input devices, such as input devices 241 and/or 242.

At a process 420, motion of the imaging device is detected. The detected motion may include a repositioning of the imaging device (e.g., a translation within the workspace), a reorienting of the imaging device (e.g., a rotation within the workspace), or a combination of a repositioning and a reorientation. In some examples, the rotation may correspond to a roll, a pitch, a yaw, and/or the like of the imaging device. In some examples, the translation may correspond to an insertion, a retraction, an upward movement, a downward movement, a leftward movement, a rightward movement, a movement as part of a pitch or yaw, and/or the like relative to an imaging device coordinate system of the imaging device. In some examples, the detected motion is the motion associated with the one or more commands used to move the imaging device in the imaging device motion mode.

At a process 430, it is determined whether the instrument is within a viewing region. In general, the instrument is considered within the viewing region when it is possible that one or more portions (e.g., a distal portion) of the instrument is visible within those portions of images captured by the imaging device so that an operator, upon viewing the images, is able to monitor the motion of the instrument to help ensure that it is safely and/or correctly moving within the workspace and is not, for example, colliding with other objects in the workspace, such as anatomy of a patient in a medical example. However, because there may also be one or more objects in the workspace (e.g., another instrument, anatomy, and/or the like) that may be obscuring some or all of the portions of the instrument that are of interest, making the determination of whether the instrument is within the viewing region is not always an easy task. Several different tests are possible.

In some examples, one test for determining whether the instrument is within the viewing region uses the kinematics of the computer-assisted device to make the determination. This test includes using one or more kinematic models of the links and joints (both shared and independent) for the repositionable structures used to move the imaging device to determine a position and an orientation of the imaging device. The position and the orientation of the imaging device are then used to determine a field of view that describes the region within the workspace that is potentially visible to the imaging device and capturable using the imaging device. In some examples, for some imaging devices, the field of view may comprise a viewing frustum. In some examples, for some imaging devices, the region that is potentially visible to the imaging device and capturable using the imaging device is a three-dimensional volume. In some examples, the field of view may be limited to extend between a configurable minimum view distance from the imaging device and a configurable maximum view distance from the imaging device. In some examples, the minimum and maximum view distances may be determined based on one or more of a focal length of the imaging device, a type of the imaging device, a type of procedure being performed, operator preference, and/or the like. In some examples, the angular spread of the field of view about a direction of view of the imaging device may be determined based on a field of view of the imaging device. In some examples, the field of view may be determined in a world coordinate system, a workspace coordinate system, an imaging device coordinate system, and/or the like.

In some embodiments, the viewing region of the images captured by the imaging device (e.g., the portions of the images displayed to the operator) may be different from the field of view. In some examples, a user interface used to display the images captured by the imaging device may include one or more controls that allow the operator to control which potions of the images captured by the imaging device form the viewing region. In some examples, the one or more controls include one or more panning, zooming, digital zooming, cropping, and/or other image transformation techniques that allow the operator to view some and/or an entirety of the images captured by the imaging device. In some examples, the viewing region may include visual information of the workspace not currently within the field of view of the imaging device, such as when one or more previously captured images and/or information from other imaging devices are used to form the images displayed to the operator. In some examples, the panning, zooming, digital zooming, cropping, and/or other image transformation techniques may be used to further transform the imaging device coordinate system to determine a viewing region coordinate system and/or determine the viewing region within the world coordinate system, the workspace coordinate system, and/or the like.

Once the viewing region is determined, the position and/or the orientation of the instrument relative to the viewing region may be determined using one or more kinematic models of the links and joints (both shared and independent links and joints) for the repositionable structures used to move the instrument. In some examples, the repositionable structures for the instrument may share one or more links and joints with the repositionable structures of the imaging device. In some examples, the position of one or more portions (e.g., a distal portion, one or more control points, and/or the like) are then mapped to the same coordinate system used to describe the viewing region to determine whether the one or more portions are partially and/or fully within the viewing region. In some examples, a portion of the instrument is considered partially within the viewing region when a static or configurable percentage (e.g., 50 percent or more) of the portion is within the viewing region.

In some examples, another test for determining whether the instrument is within the viewing region uses an external sensor or tracking system to determine the position and/or the orientation of the instrument and/or the imaging device, and then from that determine whether the one or more portions of the instrument are within the viewing region. In some examples, the tracking system may use one or more of radio frequency, ultrasound, x-ray, fluoroscopy, and/or the like to determine the position and/or the orientation of the instrument.

In some examples, another test for determining whether the instrument is within the viewing region uses a tracking system, such as a tracking system including an inertial measurement unit (IMU), to track motion of the instrument to determine the position and/or the orientation of the instrument. In some examples utilizing IMUs, information from the IMUs may be used to supplement the position and/or the orientation determinations determined from the one or more kinematic models and/or other parts of the tracking system.

In some examples, even though the one or more kinematic models, the tracking system (with or without an IMU) provide a positive indication that the instrument is within the viewing region, it is possible that the instrument is not actually visible in images captured by the imaging device and, thus, not viewable by the operator. When the instrument is not viewable by the operator it impairs the ability of the operator to monitor the motion of the instrument. Thus, in some examples, one or more images captured by the imaging device may be analyzed to determine whether the one or more portions of the instrument are within the viewing region. In some examples, one or more image processing techniques may be used that analyze the captured images to determine whether one or more fiducial markers, one or patterns, one or more shapes, and/or the like of the instrument are visible in the captured images.

In some examples, affirmative operator confirmation may be used to determine whether the instrument is within the viewing region. In some examples, the user interface, such as the user interface displayed on monitor 245, may be used by the operator to indicate whether the instrument is visible in the captured images being displayed to the operator. In some examples, the affirmative operator confirmation may include using a pointing device (e.g., a mouse, a telestrator, gaze tracking, and/or the like) to indicate whether the instrument is within the viewing region. In some examples, the operator may use a menu, a check box, a voice command, and/or the like to make the affirmative operator confirmation.

In some examples, a compound test involving one or more of the tests described above and/or other tests may be used to determine whether the instrument is within the viewing region. In some examples, when the one or more portions include multiple portions that are relevant, an aggregation may be used to make the determination. In some examples, the determination may be made separately for each of the one or more portions and then an aggregation (such as a voting technique, a weighted sum, and/or the like of the separate determinations) may be used to make the determination of whether the instrument is within the viewing region. In some examples, the weighted sum may be used to put greater emphasis on one of the portions over the other portions (e.g., a determination of whether the distal portion of the instrument is within the viewing region may be given greater weight than whether some other portion of the instrument is within the viewing region). In some examples, when one of the portions corresponds to more than just a specific point on and/or associated with the instrument, the voting weight and/or the contribution to the weighted sum for that portion may be given a contribution based on the extent (e.g., a percentage) the portion is within the viewing region.

In some examples, determination results from two or more of the tests may be aggregated together to determine whether the instrument is within the viewing region. In some examples, a voting technique, a weighted sum, and/or the like similar to that used for aggregating results for two or more portions of the instrument may be used to determine whether the instrument is within the viewing region. Other examples of techniques and/or tests for determining the position and/or the orientation of an instrument and the combining of two or more tests are described in greater detail in commonly-owned U.S. Patent Application Publication No. 2017/0079726, U.S. Pat. Nos. 8,108,072, and 8,073,528, each of which are incorporated by reference in their entirety.

In some examples, the results of any of the determinations, voting, weighed sums, and/or the like may be compared against a configurable threshold or confidence score to determine whether the determination indicates that the instrument is within the viewing region.

When it is determined that the instrument is within the viewing region, the instrument tip and/or other portions of the instrument body is moved so that it follows the imaging device using a process 440. When it is determined that the instrument is not within the viewing region ice, the instrument tip and/or other portions of the instrument body is held in place using a process 450.

At the process 440, the instrument is placed in an image-device-following mode where the instrument tip and/or other portions of the instrument body move with the imaging device. When the instrument is within the viewing region, the instrument tip and/or other portions of the instrument body are moved so that a part and/or the entirety of the instrument maintains a fixed position and/or a fixed orientation relative to the position and/or the orientation of the imaging device. In some examples, the instrument tip and/or other portions of the instrument body may correspond to the portion of the instrument used to make the determination that the instrument is within the viewing region during process 430. In this situation, the operator may use the one or more images captured by the imaging device to monitor the motion of the instrument as it moves. How the instrument tip and/or other portions of the instrument body are moved to follow the imaging device depends on the type of the links and joints used to move the imaging device. When the imaging device is being moved using just links and joints shared with the instrument, the instrument tip and/or other portions of the instrument body will naturally move along with and follow the imaging device as long as the independent links and joints of the instrument are kept unmoving relative to each other. When the imaging device is being moved using any of its independent links and joints, the motion of the imaging device due to the independent links and joints is matched by using the independent links and joints of the instrument to keep the instrument tip and/or other portions of the instrument body in the fixed position and/or orientation relative to the imaging device. Where the imaging device and the instrument have similar kinematics, this may involve the instrument tip and/or other portions of the instrument body performing the same relative motions as the independent links and joints contribute to the motion of the imaging device. In some examples, motion of the independent joints of the instrument may be commanded to move by sending one or more currents, voltages, pulse-width modulated signals and/or the like to one or more actuators used to move the independent joints. While the instrument is in the image-device-following mode, continued monitoring of the motion of the imaging device occurs by returning to process 420.

At the process 450, the instrument is placed in a hold mode where the instrument tip and/or other portions of the instrument body remain stationary in the workspace. When the instrument is not within the viewing region, the operator is not able to monitor the motion of the instrument using the one or more images captured by the imaging device. In some examples, the instrument tip and/or other portions of the instrument body may correspond to the portion of the instrument used to make the determination that the instrument is within the viewing region during process 430. How the instrument tip and/or other portions of the instrument body are kept stationary in and fixed relative to the workspace depends on the type of the links and joints used to move the imaging device. When the imaging device is being moved using just its independent links and joints, the motion of the independent links and joints of the imaging device do not cause motion in the instrument and the instrument tip and/or other portions of the instrument body may be kept stationary relative to the workspace as long as the independent links and joints of the instrument are kept unmoving relative to each other. When the imaging device is being moved using any of the links and joints it shares with the instrument (alone and/or in combination with the independent links and joints of the imaging device), the independent links and joints of the instrument are moved so as to compensate for motion of at least the instrument tip and/or other portions of the instrument body due to the motion from the shared links and joints. In some examples, motion of the independent joints of the instrument may be commanded to move by sending commands to actuator controller circuitry (e.g., a motor controller), and/or by sending one or more currents, voltages, pulse-width modulated signals and/or the like directly to one or more actuators used to move the independent joints. Examples of techniques for using one set of joints to compensate for motion due to another set of joints are described in further detail in U.S. Patent Application Publication No. 2017/0181806, which is incorporated by reference in its entirety.

At an optional process 460, one or more regathering hints are provided. Regathering refers to making a determination as to whether an instrument that is currently in the hold mode, where the instrument is being held stationary in the workspace, is to be transitioned back to the image-device-following mode, where the instrument tip and/or other portions of the instrument body move with the imaging device. In some examples, the one or more regathering hints provide information to aid in moving the imaging device so that the instrument is brought within the viewing region, so the instrument may be switched to the image-device-following mode.

In some examples, the one or more regathering hints may include placing a position hint at or around a border of the one or more images captured by the imaging device that are being displayed to the operator (e.g., on monitor 245). In some examples, the position hint indicates a direction relative to a center of view of the one or more images, such that motion of the center of view (e.g., by repositioning and/or reorienting the imaging device) in that direction is likely to bring the instrument within the viewing region. In some examples, the location of the position hint may be determined based on a position of the one or more portions of the instrument considered to be relevant to the within view determinations of process 430. In some examples, the location may be determined based on a direction between the current center of viewing region and a centroid and/or weighted centroid of the one or more portions of the instrument.

In some examples, the one or more regathering hints may include superimposing a target on the one or more captured images such that motion of the imaging device to align the center of view with the target will bring the instrument within the viewing region. In some examples, the target may include a point, a circle, a cross-hair, and/or the like. In some examples, a size of the target may be configurable. In some examples, the target may indicate a region (e.g., using a pattern, shadow, color, and/or the like superimposed on the one or more captured images) of possible centers of view where the instrument would be within the viewing region. In some examples, the location of the target and/or the region may be determined by finding one or more possible center points for the viewing region that would result in the instrument being considered within the viewing region according to the determinations of process 430.

In some examples, the one or more regathering hints may include haptic feedback on the one or more input devices (e.g., input devices 241 and/or 242) that use force and/or torque feedback to guide control of the motion of the imaging device that is likely to bring the instrument within the viewing region. In some examples, whether to apply haptic feedback that resists further control of the motion of the imaging device may be determined based on whether a velocity of the center of the viewing region indicates it is moving away from the target center of view and/or the region of possible centers of view that would allow the instrument to be considered within the viewing region according to the determinations of process 430.

In some examples, the one or more regathering hints may include a regather assist mode that automatically repositions and/or reorients the imaging device so that the center of view is aligned with the target center of view and/or the region of possible centers of view that would allow the instrument to be considered within the viewing region according to the determinations of process 430. In some examples, the regather assist mode may be activated by the operator using a user interface control, a voice command, and/or the like.

At a process 470, it is determined whether the instrument is to be regathered and switched from the hold mode to the image-device-following mode. In some examples, process 470 may be performed continuously and/or periodically during the performance of method 400. In some examples, the instrument may be regathered once it becomes within the viewing region, such as by having process 470 be substantially the same as process 430.

In some examples, the instrument may be regathered when the distal portion (or another suitable portion) of the instrument is looked at by the operator using the imaging device. In some examples, the instrument is considered looked at when the operator moves the imaging device so that the center of the viewing region is within a threshold distance of a point representative of the distal portion of the instrument as projected onto a viewing plane of the imaging device. In some examples, the representative point may be a distal end of the instrument, a centroid of the distal portion of the instrument, and/or the like. In some examples, the threshold distance may be based on a size of the one or more images captured by the imaging device. In some examples, the size may correspond to one quarter of the length of a shortest major axis (e.g., horizontal or vertical) of the one or more images. In some examples, the threshold distance may be based on a type of procedure being formed, a type of the computer-assisted device, operator preference, and/or the like.

In some examples, the instrument may be regathered in response to an affirmative regathering action by the operator. In some examples, the affirmative regathering action may be implemented similar to the affirmative operator confirmation described with respect to process 430. In some examples, the affirmative regathering action may be separate for each instrument and/or apply globally to each of the instruments in the hold mode.

In some examples, the instrument may be regathered when the instrument is brought within a configurable distance of another instrument already in the image-device-following mode. In some examples, the distance between two instruments is determined based on a distance between respective representative points on the instruments. In some examples, the respective representative points may correspond to a distal end of the respective instrument, a centroid of the distal potion of the respective instrument, a centroid of an end effector of the instrument, and/or the like. In some examples, the configurable distance is somewhere between 0.2 to 5 cm inclusive. In some examples, the configurable distance may be based on a type of procedure being formed, a type of the computer-assisted device, operator preference, an accuracy of the techniques used to determine the positions of the representative points, and/or the like. In some examples, the distance between the two representative points has to remain within the configurable distance for a configurable period of time, such as 0.5-2 s. In some examples, the configurable period of time may be based on a type of procedure being formed, a type of the computer-assisted device, operator preference, and/or the like.

In some examples, the instrument may be regathered when the instrument is touched by another instrument already in the image-device-following mode. In some examples, two instruments are considered touched when the distance between the respective representative points on the two instruments is approximately zero (e.g., less than 0.1 cm). In some examples, contact forces, position errors, velocity errors, and/or the like, such as those that be used for collision detection may be used to determine when the two instruments are considered touched. In some examples, the distances, forces, position errors, velocity errors and/or the like may be based on a type of the computer-assisted device, operator preference, an accuracy of the techniques used to determine the positions of the representative points, and/or the like. In some examples, the two instruments have to remain touched for a configurable period of time, such as 0.5-2 s. In some examples, the configurable period of time may be based on a type of procedure being performed, a type of the computer-assisted device, operator preference, and/or the like.

In some examples, two or more of the regathering techniques described above may be concurrently supported during process 470 such that any of the supported regathering techniques may be used to regather the instrument. When the instrument is regathered, it is switched to the image-device-following mode and its motion of controlled using process 440. When the instrument is not regathered, the instrument remains in the hold mode and continues to be held stationary by returning to process 450.

As discussed above and further emphasized here, FIG. 4 is merely an example which should not unduly limit the scope of the claims. One of ordinary skill in the art would recognize many variations, alternatives, and modifications. According to some embodiments, the one or more regathering hints of process 460 may be adapted to provide one or more regathering hints to aid in the regathering of two or more instruments. In some examples, the one or more regathering hints may provide regathering hints for each of the two or more instruments, such as by placing a position hint at or around the border of the one or more captured images for each of the instruments, superimposing a region and/or providing haptic feedback to a region where the center of view would allow each of the instruments to be considered within the viewing region, and/or the like. In some examples, the regather assist mode may be adapted to move to a center of view that would jointly bring each of the instruments within the viewing region (e.g., by retracting the imaging device to bring more of the workspace within the viewing region). In some examples, the one or more regathering hints may provide regathering hints for each of the instruments separately, such as by providing one or more regathering hints of different colors for different instruments, providing one or more regathering hints for each of the instruments one at a time in a sequential order. In some examples, the sequential order may provide the one or more regathering hints for an instrument that may be brought into the viewing region with a center of the viewing region that is closest to the current center of the viewing region compared to the other instruments, an instrument that may be brought into the viewing region with a center of the viewing region farthest away from the current center of the viewing region compared to the other instruments, according to an instrument priority, an instrument that is closest to a range of motion limit in one of its independent joints, an instrument that is closest to collision with an object in the workspace, and/or the like.

According to some embodiments, the decision about whether the instrument is within the viewing region may occur at other events, places, and/or times within method 400. In some examples, process 420 is optional and may be omitted such that process 430 may determine whether the instrument is within the viewing region even when no motion of the imaging device occurs. In some examples, regathering of the instrument is not permitted while the computer-assisted device remains in the imaging device motion mode. In this case, the instrument may be regathered by temporarily exiting and then reentering the imaging device motion mode. In this arrangement, process 470 is omitted, process 430 occurs concurrently with process 410, and processes 450 and 460 repeat in a loop. In some examples, the determination of whether the instrument is within the viewing region occurs each time motion of the imaging device stops and then a further motion is detected by having the "no" branch out of process 470 return to process 420 rather than process 430. In some examples, motion of the imaging device is considered stopped when a speed of motion of the imaging device, such as is detected during process 420, falls below a configurable speed threshold (e.g., 0.5-1.0 cm/s) for a configurable period of time (e.g., 0.5-2.0 s). In some examples, the configurable speed threshold and/or the period of time may be set based on a type of procedure being formed, a type of the computer-assisted device, operator preference, and/or the like.

According to some embodiments, processes 440 and/or 450 may be adapted to account for range of motion limits in the independent joints of the instrument. In some examples, when the desired motion of the instrument is being performed using independent joints of the instrument, the commanded motion for each of the independent joints may be monitored so as to avoid a range of motion in one or more of the independent joints. In some examples, the range of motion limit may correspond to a hard range of motion limit caused by a physical limitation of an independent joint or may correspond to a soft range of motion limit that is set a configurable distance short of the hard range of motion limit. In some examples, when the commanded motion of an independent joint would meet or exceed its corresponding range of motion limit an alert (e.g., audio, visual, haptic feedback, and/or the like) may be provided to the operator. In some examples, when the commanded motion of an independent joint would meet or exceed its corresponding range of motion limit, the imaging device motion mode is exited so that further motion of the imaging device is not permitted. In some examples, haptic feedback may be used to resist further motion of the one or more input devices (e.g., input devices 241 and/or 242) used to control the imaging device so that further motion of the imaging device that would cause one of the independent joints of the instrument to exceed the range of motion limit would be actively resisted. In some examples, when the operator applies excessive force and/or torque to the one or more input devices against the haptic feedback (e.g., above a configurable force and/or torque for a configurable minimum duration), the instrument could be automatically regathered (e.g., by switching the instrument to the image-device-following mode) and/or temporarily regathering the instrument until the range of motion limit for the independent joint is no longer exceeded and then the instrument may be returned to the hold mode. In some examples, range of motion limit hints may also be displayed to the operator (e.g., on the user interfaced displayed on monitor 245). In some examples, the range of motion limits may indicate one or more regions where the center of the viewing region could not be moved without causing a range of motion limit issue in an independent joint of the instrument, would cause the imaging device and/or the instrument to enter a no-fly region where the imaging device or the instrument is not permitted, a collision with one or more objects in the workspace, and/or the like. In some examples, the region may be indicated by superimposing one or more of a color, a shadow, a pattern, and/or the like on the one or more images captured by the imaging device.

Some examples of control units, such as control unit 140 and/or operator console 240 may include non-transitory, tangible, machine readable media that include executable code that when run by one or more processors (e.g., processor 150 and/or processor 243) may cause the one or more processors to perform the processes of method 400. Some common forms of machine readable media that may include the processes of method 400 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and, in a manner, consistent with the scope of the embodiments disclosed herein.

What is claimed is:

1. A computer-assisted device comprising:

a first manipulator configured to support a first instrument that includes an imaging device;

a second manipulator configured to support a second instrument;

a memory storing instructions; and a controller coupled to the first and second manipulators;

wherein while the computer-assisted device is in an imaging device motion mode, the controller executes the instructions to perform operations comprising:

determining that an event has occurred, the event corresponding to a movement of the imaging device or a command to move the imaging device relative to an imaging device coordinate system of the imaging device, and while the event is occurring:

capturing an image of a workspace using the imaging device, determining that a first portion of the second instrument is within a viewing region of the captured image, in response to determining that the first portion of the second instrument is within the viewing region while the event occurs, causing the computer-assisted device to command the second manipulator to move the second instrument in response to the event, so that a second portion of the second instrument is maintained in a fixed position relative to a position of the imaging device in response to the event, and in response to determining that the first portion of the second instrument is not within the viewing region while the event occurs, commanding the second manipulator to keep the position of the second portion of the second instrument fixed relative to the workspace in response to the event.

2. The computer-assisted device of claim 1, wherein:

the first portion is a distal portion or a distal end of the second instrument; or the position of the second portion of the second instrument comprises a position of a distal portion of the second instrument, of a distal end of the second instrument, or of the first portion of the second instrument.

3. The computer-assisted device of claim 1, wherein determining that the first portion of the second instrument is within the viewing region of the captured image further comprises:

determining an extent of a field of view of the imaging device based on one or more kinematic models of the first manipulator and the first instrument; or using one or more kinematic models of the second manipulator and the second instrument to map the first portion to a coordinate system associated with the viewing region; or tracking the second instrument using a tracking system; or analyzing the image to detect one or more of the first portion, a fiducial marker, a pattern, or a shape of the second instrument.

4. The computer-assisted device of claim 1, wherein determining that the first portion of the second instrument is within the viewing region of the captured image further comprises:

determining how much of the first portion is within the viewing region; or determining a portion of the captured image being displayed to an operator.

5. The computer-assisted device of claim 1, wherein the controller further executes the instructions to perform operations comprising:

determining whether a third portion of the second instrument is within the viewing region; and in response to determining that the third portion of the second instrument is not within the viewing region, commanding the second manipulator to keep the position of the second portion of the second instrument fixed relative to the workspace in response to the event.

6. The computer-assisted device of claim 1, wherein determining that the first portion of the second instrument is within the viewing region of the captured image is performed in response to at least one event selected from the group consisting of:

an entry into the imaging device motion mode;

a detection of motion of the imaging device; or a passage of a period of non-motion of the imaging device.

7. The computer-assisted device of claim 1, wherein the controller switches from keeping the position of the second portion of the second instrument fixed relative to the workspace to keeping the position of the second portion of the second instrument fixed relative to the position of the imaging device when:

a center of the viewing region becomes within a threshold distance of the first portion of the second instrument; or the first portion of the second instrument becomes located in a central region of the viewing region.

8. The computer-assisted device of claim 1, wherein the controller further executes the instructions to perform operations comprising:

keeping a third portion of a third instrument fixed relative to the position of the imaging device when keeping the position of the second portion of the second instrument fixed relative to the workspace; and switching, from keeping the position of the second portion of the second instrument fixed relative to the workspace to keeping the position of the second portion of the second instrument fixed relative to the position of the imaging device, in response to at least one event selected from the group consisting of: the first portion of the second instrument touching the third instrument and the first portion of the second instrument becoming within a threshold distance of the third instrument.

9. The computer-assisted device of claim 1, wherein when the position of the second portion of the second instrument is being kept fixed relative to the workspace, the controller provides one or more hints for bringing the first portion within the viewing region.

10. The computer-assisted device of claim 9, wherein the one or more hints comprise at least one hint selected from the group consisting of: a position hint near a border of the image, a target for a center of the viewing region overlaid on the image, a region of possible centers of the viewing region overlaid on the image, and haptic feedback.

11. The computer-assisted device of claim 1, wherein the controller, while keeping the position of the second portion of the second instrument fixed relative to the workspace, repositions the imaging device, reorients the imaging device, or both repositions and reorients the imaging device to bring the first portion of the second instrument into the viewing region in response to a command from an operator.

12. The computer-assisted device of claim 1, wherein the controller, while commanding the second manipulator to keep the position of the second portion of the second instrument fixed relative to the workspace, further executes the instructions to perform operations comprising:

determining that further motion of the imaging device will result in a joint of the second manipulator or the second instrument reaching a range of motion limit; and in response to determining that the further motion of the imaging device will result in the joint of the second manipulator or the second instrument reaching the range of motion limit, providing an alert, providing haptic feedback, or exiting the imaging device motion mode.

13. The computer-assisted device of claim 1, wherein causing the computer-assisted device to command the second manipulator to move the second instrument so that the second portion of the second instrument is maintained in a fixed position relative to the position of the imaging device further comprises:

in response to detecting that a motion of the imaging device is due to motion in one or more independent joints of the first instrument or the first manipulator, sending one or more commands to one or more independent joints of the second instrument or the second manipulator to move the second instrument to match the motion of the imaging device; or in response to detecting that a motion of the imaging device is due to motion in one or more joints shared between the imaging device and the second instrument, preventing motion of one or more independent joints of the second instrument or the second manipulator.

14. The computer-assisted device of claim 1, wherein to keep the position of the second portion of the second instrument fixed relative to the workspace, the controller further executes the instructions to perform operations comprising:

in response to detecting that a motion of the imaging device is due to motion in one or more independent joints of the first instrument or the first manipulator, preventing motion of one or more independent joints of the second instrument or the second manipulator; or in response to detecting that a motion of the imaging device is due to motion in one or more joints shared between the imaging device and the second instrument, sending one or more commands to one or more independent joints of the second instrument or the second manipulator to move the second portion of the second instrument to counteract the motion of the one or more joints shared between the imaging device and the second instrument.

15. The computer-assisted device of claim 1, further comprising:

a first shared link or joint;

wherein the first manipulator is coupled to the first shared link or joint at a proximal end of the first manipulator, and the second manipulator is also coupled to the first shared link of joint at a proximal end of the second manipulator;

wherein, when the computer-assisted device is in the imaging device motion mode, the controller causes the imaging device to move using the first shared link or joint.

16. A method of operating a computer-assisted device in an imaging device motion mode, the method comprising:

determining, by a controller, that an event has occurred, the event corresponding to a movement of an imaging device or a command to move the imaging device relative to an imaging device coordinate system of the imaging device, and while the event is occurring:

determining, by the controller, that a first portion of an instrument supported by a first manipulator of the computer-assisted device is within a viewing region of an image captured by the imaging device supported by a second manipulator of the computer-assisted device;

in response to determining that the first portion of the instrument is within the viewing region while the event occurs, causing, by the controller, the computer-assisted device to command the first manipulator to move the instrument in response to the event, so that a second portion of the instrument is maintained in a fixed position relative to a position of the imaging device in response to the event; and in response to determining that the first portion of the instrument is not within the viewing region while the event occurs, commanding, by the controller, the first manipulator to keep the position of the second portion of the instrument fixed relative to a workspace in response to the event.

17. The method of claim 16, wherein determining, by the controller, that the first portion of the instrument is within the viewing region further comprises:

determining how much of the first portion is within the viewing region; or determining a portion of the captured image being displayed to an operator.

18. The method of claim 16, wherein determining, by the controller, that the first portion of the instrument is within the viewing region is performed in response to at least one event selected from the group consisting of:

an entry into the imaging device motion mode;

a detection of a motion of the imaging device; or a passage of a period of non-motion of the imaging device.

19. The method of claim 16, further comprising switching, by the controller, from keeping the position of the second portion of the instrument fixed relative to the workspace to keeping the position of the second portion of the instrument fixed relative to the position of the imaging device when:

a center of the viewing region becomes within a threshold distance of the first portion of the instrument; or the first portion of the instrument becomes located in a central region of the viewing region.

20. The method of claim 16, further comprising:

keeping, by the controller, a third portion of a second instrument fixed relative to the position of the imaging device when keeping the position of the second portion of the instrument fixed relative to the workspace; and switching, by the controller, from keeping the position of the second portion of the instrument fixed relative to the workspace to keeping the position of the second portion of the instrument fixed relative to the position of the imaging device, in response to at least one event selected from the group consisting of: the first portion of the instrument touching the second instrument and the first portion of the instrument becoming within a threshold distance of the second instrument.

21. The method of claim 16, wherein when the position of the second portion of the instrument is being kept fixed relative to the workspace, the method further comprises:

providing, by the controller, one or more hints for bringing the first portion within the viewing region.

22. The method of claim 16, further comprising, while keeping the position of the second portion of the instrument fixed relative to the workspace, repositioning, by the controller, the imaging device, reorienting, by the controller, the imaging device, or both repositioning and reorienting, by the controller, the imaging device to bring the first portion of the instrument into the viewing region in response to a command from an operator.

23. The method of claim 16, further comprising, while commanding the first manipulator to keep the position of the second portion of the instrument fixed relative to the workspace:

determining, by the controller, that further motion of the imaging device will result in a joint of the first manipulator or the instrument reaching a range of motion limit; and in response to determining that the further motion of the imaging device will result in the joint of the first manipulator or the instrument reaching the range of motion limit, providing an alert, providing, by the controller, haptic feedback, or exiting the imaging device motion mode.

24. A non-transitory machine-readable medium comprising a plurality of machine-readable instructions which, when executed by one or more processors, cause the one or more processors to:

determine that an event has occurred, the event corresponding to a movement of an imaging device or a command to move the imaging device relative to an imaging device coordinate system of the imaging device, and while the event is occurring:

determine that a first portion of an instrument supported by a first manipulator of a computer-assisted device is within a viewing region of an image captured by the imaging device supported by a second manipulator of the computer-assisted device;

in response to determining that the first portion of the instrument is within the viewing region while the event occurs, cause the computer-assisted device to command the first manipulator to move the instrument in response to the event, so that a second portion of the instrument is maintained in a fixed position relative to a position of the imaging device in response to the event; and in response to determining that the first portion of the instrument is not within the viewing region while the event occurs, command the first manipulator to keep the position of the second portion of the instrument fixed relative to a workspace in response to the event.

25. The non-transitory machine-readable medium of claim 24, wherein determining that the first portion of the instrument is within the viewing region occurs:

at entry into an imaging device motion mode;

in response to detecting motion of the imaging device; or in response to a passage of a period of non-motion of the imaging device.

26. The non-transitory machine-readable medium of claim 24, wherein the plurality of machine-readable instructions, when executed by the one or more processors, further cause the one or more processors to: switch from keeping the position of the second portion of the instrument fixed relative to the workspace to keeping the position of the second portion of the instrument fixed relative to the position of the imaging device in response to at least one event selected from the group consisting of:

a center of the viewing region becoming within a threshold distance of the first portion of the instrument;

the first portion of the instrument becoming located in a central region of the viewing region;

the first portion of the instrument touching a second instrument; and the first portion of the instrument becoming located within a threshold distance of the second instrument.

* * * * *